US00PP32332P3

(12) United States Plant Patent
Raadschelders

(10) Patent No.: US PP32,332 P3
(45) Date of Patent: Oct. 13, 2020

(54) ***PHLEBODIUM* PLANT NAMED 'RAADPHLE01'**

(50) Latin Name: ***Phlebodium aureum* (L.) J. Sm.**
Varietal Denomination: RAADPHLE01

(71) Applicant: Raadschelders Varens B. V., De Kwakel (NL)

(72) Inventor: Kelly Raadschelders, De Kwakel (NL)

(73) Assignee: Raadschelders Varens B. V., De Kwakel (NL)

( * ) Notice: Subject to any disclaimer, the term of this patent is extended or adjusted under 35 U.S.C. 154(b) by 0 days.

(21) Appl. No.: 16/602,725

(22) Filed: Nov. 27, 2019

(65) Prior Publication Data

US 2020/0178451 P1 Jun. 4, 2020

(30) Foreign Application Priority Data

Nov. 29, 2018 (QZ) ..... PBR 2018/3132

(51) Int. Cl.
*A01H 9/00* (2006.01)

(52) U.S. Cl.
USPC ..... Plt./379
CPC ..... *A01H 9/00* (2013.01)

(58) Field of Classification Search
USPC ..... Plt./379
CPC ..... A01H 9/00
See application file for complete search history.

*Primary Examiner* — Keith O. Robinson
(74) *Attorney, Agent, or Firm* — Samuel R. McCoy, Jr.

(57) ABSTRACT

A new and distinct *Phlebodium* plant named 'RAADPHLE01' which is characterized by an upright to arching growth habit, an abundance of light yellow-green juvenile fronds and dark green mature fronds, lobed fronds with crenulate margins that are strongly undulate, and the stability of these characteristics from generation to generation.

2 Drawing Sheets

Latin name of the genus and species: The Latin name of the genus and species of the novel variety disclosed herein is *Phlebodium aureum* (L.) J. Sm.

Variety denomination: The inventive variety of *Phlebodium* disclosed herein has been given the variety denomination 'RAADPHLE01'.

CROSS REFERENCE TO RELATED APPLICATIONS

This application claims priority to the Community Plant Variety Rights application number 2018/3132, filed Nov. 29, 2018, which is herein incorporated by reference.

BACKGROUND OF THE INVENTION

Parentage: 'RAADPHLE01' is a spontaneous whole-plant mutation which was discovered growing amongst a cultivated population of *Phlebodium aureum* 'Blue Star' (not patented) which was discovered by the inventor in January of 2015 at a commercial greenhouse in De Kwakel, the Netherlands. The mutation was first noted for its leaves which are shallowly to moderately lobed and strongly undulate compared to those of the parent plant.

Asexual Reproduction: Asexual reproduction of the new cultivar 'RAADPHLE01', by way of meristematic tissue culture, was first initiated in October of 2015 at a tissue culture laboratory in Burgh Haamstede, the Netherlands. Through two subsequent generations, the unique features of this cultivar have proven to be stable and true to type.

SUMMARY OF THE INVENTION

The cultivar 'RAADPHLE01' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'RAADPHLE01'. These characteristics in combination distinguish 'RAADPHLE01' as a new and distinct *Phlebodium* cultivar:

1. *Phlebodium* 'RAADPHLE01' exhibits an upright to arching growth habit with an abundance of fronds; and
2. *Phlebodium* 'RAADPHLE01' exhibits light yellow-green juvenile fronds which are covered with a thin layer of greyed-green epicuticular wax; and
3. *Phlebodium* 'RAADPHLE01' exhibits dark green mature fronds which are covered with a thin layer of greyed-green epicuticular wax; and
4. *Phlebodium* 'RAADPHLE01' exhibits fronds which are shallowly to moderately lobed with parallel to divergent sinuses.
5. *Phlebodium* 'RAADPHLE01' exhibits fronds margins are strongly undulate.

BOTANICAL DESCRIPTION OF THE PLANT

Figure 1:
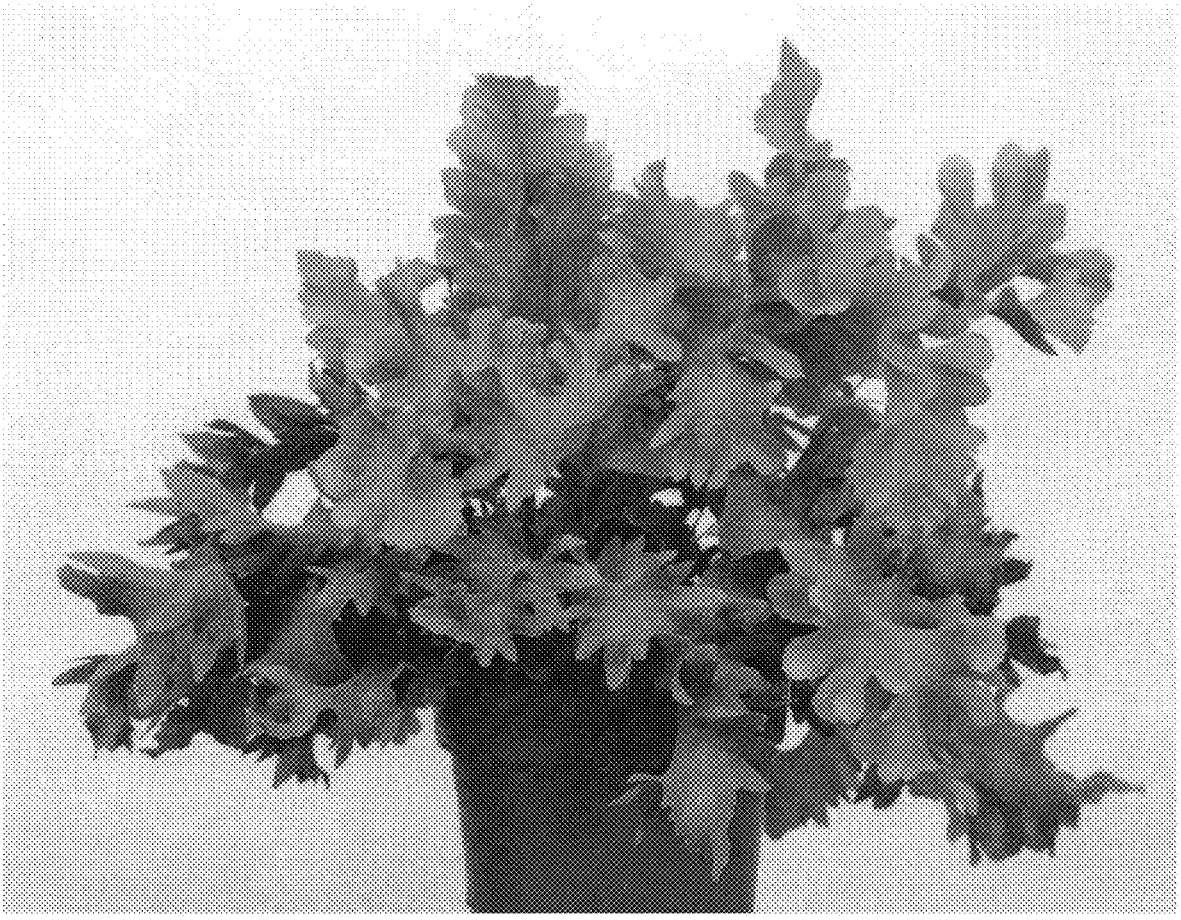
FIG. 1 illustrates, as nearly true as it is reasonably possible to make the same in color photographs of this type, an exemplary plant of 'RAADPHLE01' grown in a commercial greenhouse in Burgh Haamstede, the Netherlands. This plant is approximately 30 week-old, shown planted in a 12 cm container.
Figure 2:
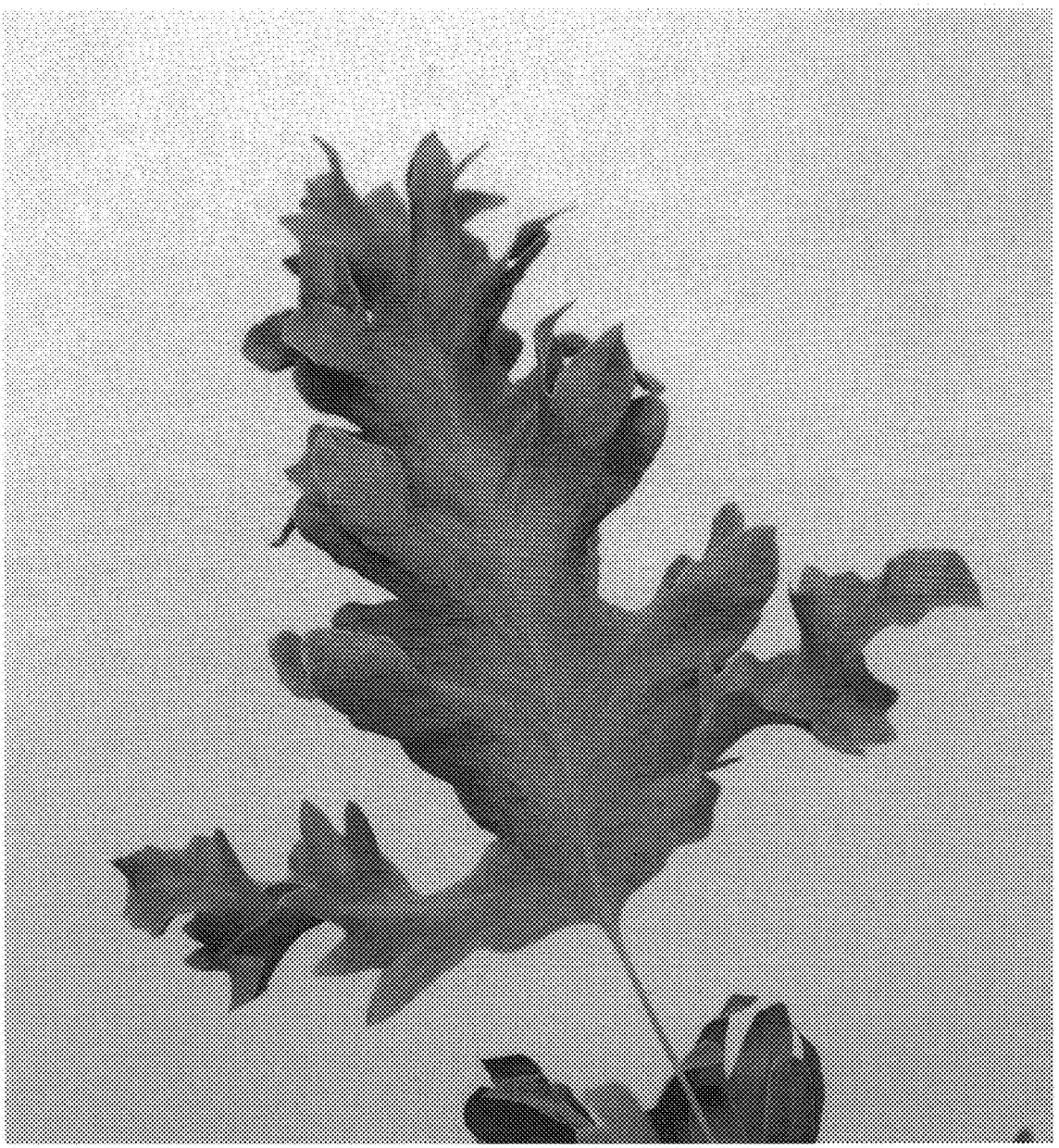
FIG. 2 illustrates, as nearly true as it is reasonably possible to make the same in color photographs of this type, the typical fronds of 'RAADPHLE01'.

The following observations and measurements made in June of 2019 describe averages from a sample set of six specimens of 30 week-old 'RAADPHLE01' plants grown in 12 cm nursery containers at a greenhouse in Burgh Haamstede, the Netherlands. Plants were produced using conventional greenhouse production protocols which consisted of ebb and flow irrigation benches, shade cover, and liquid fertilizer applications. No photoperiodic or pesticide treatments or artificial light was given to the plants.

Those skilled in the art will appreciate that certain characteristics will vary with older or, conversely, with younger plants. 'RAADPHLE01' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'RAADPHLE01' and a comparison with the parent plant and most similar commercial variety known to the inventor are provided below.

Plant description:

*Growth habit*.—Herbaceous perennial fern with an upright to arching growth habit; leaves growing from a basal rhizomes.

*Plant shape*.—Flattened globular.

*Height from soil level to top of foliar plane*.—19.9 cm.

*Plant spread*.—Average of 37.6 cm.

*Growth rate*.—Moderate.

*Plant vigor*.—Moderately to highly vigorous.

*Propagation*.—Type — Mericloning. Crop time — Approximately 42 days to initiate rooting; 20 weeks from rooting to a marketable 12 cm container plant.

*Disease and pest resistance or susceptibility*.—Neither susceptibility nor resistance to pests and diseases common to *Phlebodium* sp. have been observed.

*Environmental tolerances*.—Adapt to, at least, USDA Zones 10 to 13 and temperatures as high as 35 degrees Celsius; high tolerance to rain; moderate tolerance to wind.

Root system:

*General*.—Creeping rhizomes which are very densely covered with a soft pubescence.

*Length*.—2.3 cm.

*Diameter*.—0.7 cm.

*Texture*.—Densely pubescent; covered with a soft pubescence of hairy scales. The average length of scales is 0.4 cm.

*Color*.—Greyed-green, nearest to 190A; pubescence is colored greyed-orange, nearest to a combination of RHS 164C and 164D.

Fronds:

*Arrangement*.—Alternate; growing from creeping basal rhizomes.

*Attachment*.—Petiolate.

*Division*.—Simple.

*Dimensions*.—14.3 cm long and 15.0 cm wide, on average.

*Shape*.—Hastate.

*Aspect*.—Flat with leaf apices curled downward at an average angle of 30 degrees to vertical.

*Attitude*.—At an average angle of 70 degrees to vertical; older fronts are relaxed at an average angle of minus−30 degrees to vertical.

*Apex*.—Acute to broad acute.

*Base*.—Short attenuate.

*Margin*.—Crenulate and shallowly to moderately lobed with parallel to divergent sinuses; leaves are strongly undulate.

*Pubescence and texture and luster of adaxial surface*.—Glabrous, smooth, and glossy.

*Pubescence, texture and luster of abaxial surface*.—Glabrous and smooth, with the exception of the vein axils at the base of the frond which exhibit small tufts of hair; hairs are 0.2 cm long on average and are colored yellow-white, nearest to RHS 158D.

*Luster of adaxial surface*.—Matte.

*Luster of abaxial surface*.—Matte.

*Color*.—Juvenile frond, adaxial surface — Yellow-green, nearest to RHS 144A, and covered with a thin layer of greyed-green epicuticular wax, nearest to RHS 188B. Juvenile frond, abaxial surface — Yellow-green, nearest to RHS 144B, and covered with a thin layer of greyed-green epicuticular wax, nearest to RHS 188B. Mature frond, adaxial surface — Green, nearest to RHS 137A, and covered with a thin layer of greyed-green epicuticular wax, nearest to RHS 189B. Mature frond, abaxial surface — Green, nearest to RHS 137B, and covered with a thin layer of greyed-green epicuticular wax, nearest to RHS 189B.

*Venation*.—Pattern — Pinnate. Venation color, adaxial surface — Yellow-green, nearest to RHS 147A. Venation color, abaxial surface — Yellow-green, nearest to RHS 147A.

*Petiole*.—Length — 12.1 cm. Diameter — 0.75 cm. Strength — Strong. Pubescence, texture and luster — Glabrous, smooth, and glossy. Color, adaxial surface — Yellow-green, nearest to RHS 146A. Color, abaxial surface — Yellow-green, nearest to RHS 146A.

Sori: No sori present.

COMPARISONS WITH THE PARENT PLANTS

Plants of the new cultivar 'RAADPHLE01' differ from the parent, *Phlebodium aureum* 'Blue Star' (unpatented), which is also the closest known commercial comparator, in the characteristics described in Table 1 below.

TABLE 1

| Characteristic | 'RAADPHLE01' | 'Blue Star' |
|---|---|---|
| Growth habit. | More arching than 'Blue Star'. | More upright than 'RAADPHLE01'. |
| General coloration of the mature frond. | Darker green than 'Blue Star'. | Lighter green than 'RAADPHLE01'. |
| Frond margins. | Crenulate and undulated. | Entire and undulated. |

That which is claimed is:

1. A new and distinct variety of *Phlebodium* plant named 'RAADPHLE01', substantially as described and illustrated herein.

* * * * *